(12) United States Patent
Fateh et al.

(10) Patent No.: US 6,345,893 B2
(45) Date of Patent: Feb. 12, 2002

(54) ERGONOMIC SYSTEMS AND METHODS FOR OPERATING COMPUTERS

(75) Inventors: Sina Fateh, Sunnyvale; James F. Flack, Los Alto Hills, both of CA (US)

(73) Assignee: Vega Vista, Inc., Mountain View, CA (US)

( * ) Notice: Subject to any disclaimer, the term of this patent is extended or adjusted under 35 U.S.C. 154(b) by 0 days.

(21) Appl. No.: 09/734,835

(22) Filed: Dec. 12, 2000

Related U.S. Application Data

(63) Continuation of application No. 09/476,921, filed on Jan. 4, 2000, now Pat. No. 6,244,711, which is a continuation of application No. 09/097,876, filed on Jun. 15, 1998, now Pat. No. 6,076,928.

(51) Int. Cl.$^7$ .................................................. A61B 3/14
(52) U.S. Cl. ...................................................... 351/208
(58) Field of Search ................................ 351/203, 206, 351/208, 209; 434/43, 44; 345/118, 139, 157, 162, 167, 158, 418, 440, 121

(56) References Cited

U.S. PATENT DOCUMENTS

| | | |
|---|---|---|
| 2,270,069 A | 1/1942 | Martin |
| 3,388,646 A | 6/1968 | Sullivan |
| 3,468,545 A | 9/1969 | Anderson |
| 3,582,189 A | 6/1971 | Moritz |
| 3,917,278 A | 11/1975 | Steinman |
| 4,067,129 A | 1/1978 | Abramson et al. |
| 4,068,230 A | 1/1978 | Schneiter |
| 4,137,566 A | 1/1979 | Haas et al. |
| 4,294,522 A | 10/1981 | Jacobs ........................... 351/2 |
| 4,365,873 A | 12/1982 | Ginsburg |
| 4,611,893 A | 9/1986 | Schrier |

(List continued on next page.)

OTHER PUBLICATIONS

Software Manual for Eye Works 1.0, ICC Group Inc. 1995.
Orthoptic Treatment, Chapter 18, pp. 178–201.
Health and Vision "Solving Vision Problems at Computers in the United States," Points de vue N_33, Oct. 1995.
Prio Corporation, "Latest Press Materials," http://www.prio.com, Jun. 13, 1997.
"A Vision Theraphy Software—Eyeworks," http://www.iccgroup.com.Jul. 25, 1996.

Primary Examiner—George Manuel
(74) Attorney, Agent, or Firm—Oppenheimer Wolff & Donnelly LLP

(57) ABSTRACT

The teachings of the present invention aid a user in attaining an ergonomic position with respect to a remote object such as a display screen (e.g., VDT) or a manufacturing tool. To that end, various mechanisms which feedback to the viewer information related to position and orientation are taught. A first aspect incorporates a feedback mechanism into a display screen. The feedback mechanism could be formed in a variety of manners. In one embodiment, four lights are arranged such that a viewer in the proper orientation will perceive all four lights. However, as the viewer's orientation varies, one or more of the lights is concealed, thereby indicating to the user that the orientation is improper. In another embodiment, the cluster of lights is replaced with a cluster of four distinct pieces of diffraction grating. The diffraction grating could be such that the intensity of the reflected light varies as the viewer's orientation varies. Alternatively, a hologram could arranged such that the image presented to the viewer changes, even presenting informative text to the viewer. Another aspect of the present invention teaches a feedback mechanism that further provides visual feedback regarding position information. In one embodiment, a strip of diffraction grating or other suitable material is applied upon the display screen. The strip is formed such that depending upon the viewers position, the viewer perceives a certain image (e.g., "20 Inches," the color green).

20 Claims, 8 Drawing Sheets

U.S. PATENT DOCUMENTS

| | | |
|---|---|---|
| 4,714,428 A | 12/1987 | Bunker et al. ............... 434/43 |
| 4,716,469 A | 12/1987 | Kim et al. |
| 4,831,448 A | 5/1989 | Park |
| 4,944,572 A | 7/1990 | Young |
| 5,051,931 A | 9/1991 | Cheu et al. |
| 5,133,050 A * | 7/1992 | George et al. ............. 345/632 |
| 5,252,950 A | 10/1993 | Saunders et al. |
| 5,289,220 A | 2/1994 | Fidler et al. |
| 5,311,220 A | 5/1994 | Eichenlaub |
| 5,322,441 A | 6/1994 | Lewis et al. |
| 5,351,963 A | 10/1994 | Baek |
| 5,359,675 A | 10/1994 | Siwoff |
| 5,442,734 A | 8/1995 | Murakami et al. ......... 395/127 |
| 5,452,516 A | 9/1995 | Schegerin |
| 5,510,893 A | 4/1996 | Suzuki |
| 5,515,069 A | 5/1996 | Dillon, III |
| 5,570,301 A | 10/1996 | Barrus |
| 5,579,026 A | 11/1996 | Tabata ........................ 345/8 |
| D376,648 S | 12/1996 | Fateh |
| 5,661,539 A | 8/1997 | Sheedy |
| 5,668,622 A | 9/1997 | Charbonnier et al. |
| 5,686,940 A | 11/1997 | Kuga ....................... 345/156 |
| 5,696,995 A | 12/1997 | Huang et al. ................ 396/2 |
| 5,748,228 A | 5/1998 | Kobayashi et al. |
| 5,777,715 A | 7/1998 | Kruegle et al. ............ 351/158 |
| 6,094,190 A * | 7/2000 | Kodim ..................... 345/167 |

* cited by examiner

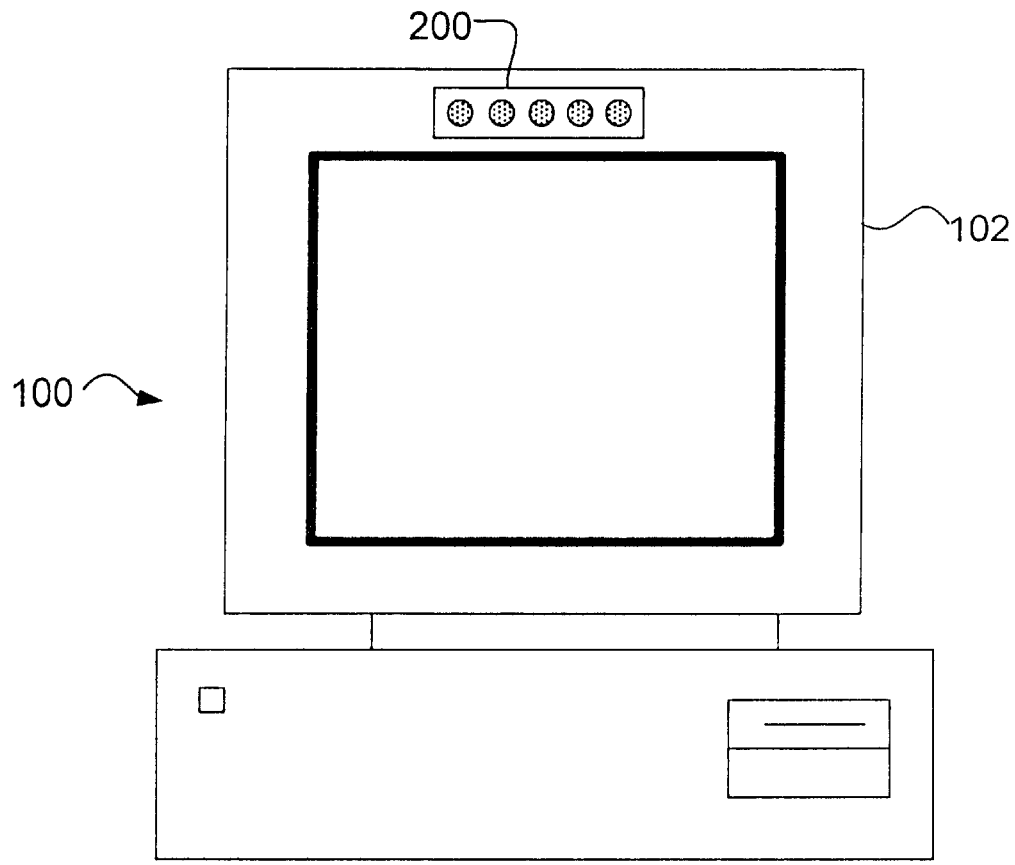
Fig. 6
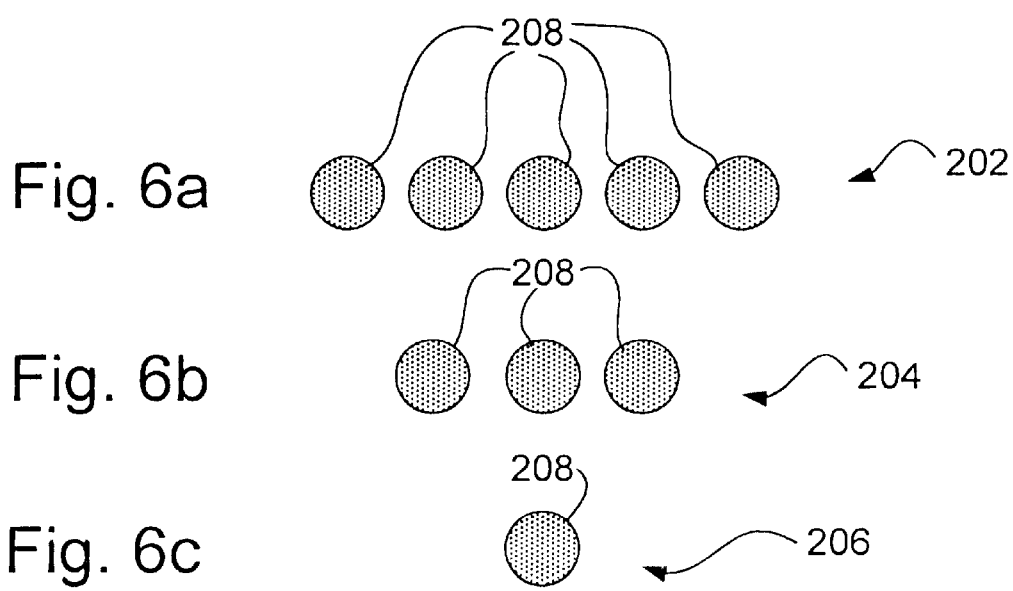
Fig. 6a
Fig. 6b
Fig. 6c

ERGONOMIC SYSTEMS AND METHODS FOR OPERATING COMPUTERS

This is Continuation of application Ser. No. 09/476,921, filed Jan. 1, 2000 now U.S. Pat. No. 6,244,711, which is a continuation of application Ser. No. 09/097,876 filed on Jun. 15, 1998 now U.S. Pat. No. 6,076,928, the disclosure of which is incorporated herein by reference.

TECHNICAL FIELD

The present invention generally relates to the field of ergonomic work environments. More specifically, the present invention teaches methods and systems for aiding a computer user in finding an ergonomic position within a work environment.

BACKGROUND

Whether working or relaxing, a growing proportion of the world's population spends prolonged periods in fixed, sedentary positions, with their vision and attention focused on a small portion of their environment. For example, office workers are required to work at computer terminals performing tasks such as word processing, data entry, and generating computer graphics. Students are regularly using computers for study and in the classroom. Computers and televisions are commonly viewed for entertainment and information purposes. These types of activities have unintended side effects such as eye fatigue, eye strain, difficulty focusing, headaches, backaches, and general muscular discomfort.

These and other symptoms are often the result of an improper arrangement of the sufferer's environment and his position and orientation within that environment. Often, steps the sufferer may take to alleviate one symptom may in turn cause other, perhaps more subtle, problems. For example, a video display terminal (VDT) user may position himself in a certain manner to avoid back discomfort, yet in so doing end up an improper distance from the VDT, as well as poorly oriented, thereby causing eye fatigue.

James E. Sheedy, in his U.S. Pat. No. 5,661,539, described what he termed a "Visual Tool for Assessing the Ergonomic Position of a Video Display Terminal." Sheedy's Visual Tool consists of a substantially planar measurement tool having a plurality of measurement indicia arranged to indicate the distance above and below a center point of the measurement tool. An alignment indicator, essentially a fabric tape measure, is attached to the center point and can be grasped by a user and extended outward. A VDT user may position the measurement tool over the face of the VDT and then determine a desired vertical orientation and distance from the face of the VDT by use of the Visual Tool. Hence Sheedy's Visual Tool provides the VDT user one manual device for determining his or her position and orientation in front of the VDT. Note, however, that the VDT use cannot simultaneously view the VDT while using Sheedy's Visual Tool.

What are needed are tools for providing a user dynamic visual feedback enabling the use to obtain a proper, ergonomic orientation with the computer work environment.

SUMMARY OF THE INVENTION

The teachings of the present invention aid a user in attaining an ergonomic position with respect to a remote object such as a display screen (e.g., VDT) or a manufacturing tool. To that end, various mechanisms which feedback to the viewer information related to position and orientation are taught. A first aspect incorporates a feedback mechanism into a display screen. The feedback mechanism could be formed in a variety of manners. In one embodiment, four lights are arranged such that a viewer in the proper orientation will perceive all four lights. However, as the viewer's orientation varies, one or more of the lights is concealed, thereby indicating to the user that the orientation is improper. In another embodiment, the cluster of lights is replaced with a cluster of four distinct pieces of diffraction grating. The diffraction grating could be such that the intensity of the reflected light varies as the viewer's orientation varies. Alternatively, a hologram could arranged such that the image presented to the viewer changes, even presenting informative text to the viewer.

Another aspect of the present invention teaches a feedback mechanism that further provides visual feedback regarding position information. In one embodiment, a strip of diffraction grating or other suitable material is applied upon the display screen. The strip is formed such that depending upon the viewers position, the viewer perceives a certain image (e.g., "20 Inches," the color green). In preferred embodiments, the left and right eyes perceive different images such that when the viewer's orientation is improper, the image perceived by one eye is different from the other.

Yet another aspect of the present invention is directed towards ergonomic software capable of executing on a computer system having a sensor capable of measuring the distance between a viewer and a display screen of the computer system. The ergonomic software measures and displays the viewers setback from the display screen, as well as making suggestions regarding preferred font size and viewer position.

BRIEF DESCRIPTION OF THE DRAWINGS

The invention, together with further objectives and advantages thereof, may best be understood by reference to the following description taken in conjunction with the accompanying drawings which are described below.

FIG. 3a illustrates a computer user positioned at an orientation above the ideal vertical ergonomic position.

FIG. 3b illustrates an image of the visual feedback device of FIG. 2 as perceived by a computer user oriented as shown in FIG. 3a.

FIG. 4a illustrates a computer user positioned at an orientation below the ideal vertical ergonomic position.

FIG. 4b illustrates an image of the visual feedback device of FIG. 2 as perceived by a computer user oriented as shown in FIG. 4a.

FIG. 5b illustrates an image of the visual feedback device of FIG. 2 as perceived by a computer user oriented as shown in FIG. 5a.

FIG. 6 illustrates a computer system having a visual feedback device in accordance with yet another embodiment of the present invention, the visual feedback device capable of rendering different images dependent upon the distance of the computer user from the computer system.

FIGS. 6a–6c illustrate three different images the computer user will perceive at three different distances from the visual feedback device of FIG. 6.

BEST MODES FOR CARRYING OUT THE INVENTION

The methods and systems of the present invention enable a user to maintain an ergonomic position with respect to a remote object such as a display screen (e.g., VDT) or a manufacturing tool. Failure to achieve a proper position and orientation of a user's viewpoint with respect to a VDT, tool position, calibrated indicator, etc., often causes physical discomfort such as eye fatigue, back strain, etc. The present invention is directed towards simple mechanisms which provide the user meaningful feedback related to both his position and orientation. In the following description of various aspects of the present invention, the VDT example is often used for ease of reference. However, those of skill in the art will recognize that the present invention is not limited by this particular application, but is suitable for other applications such as television displays, tool position indicators, status readouts or any environment wherein a viewer wishes to maintain a particular position.

Figure 1:
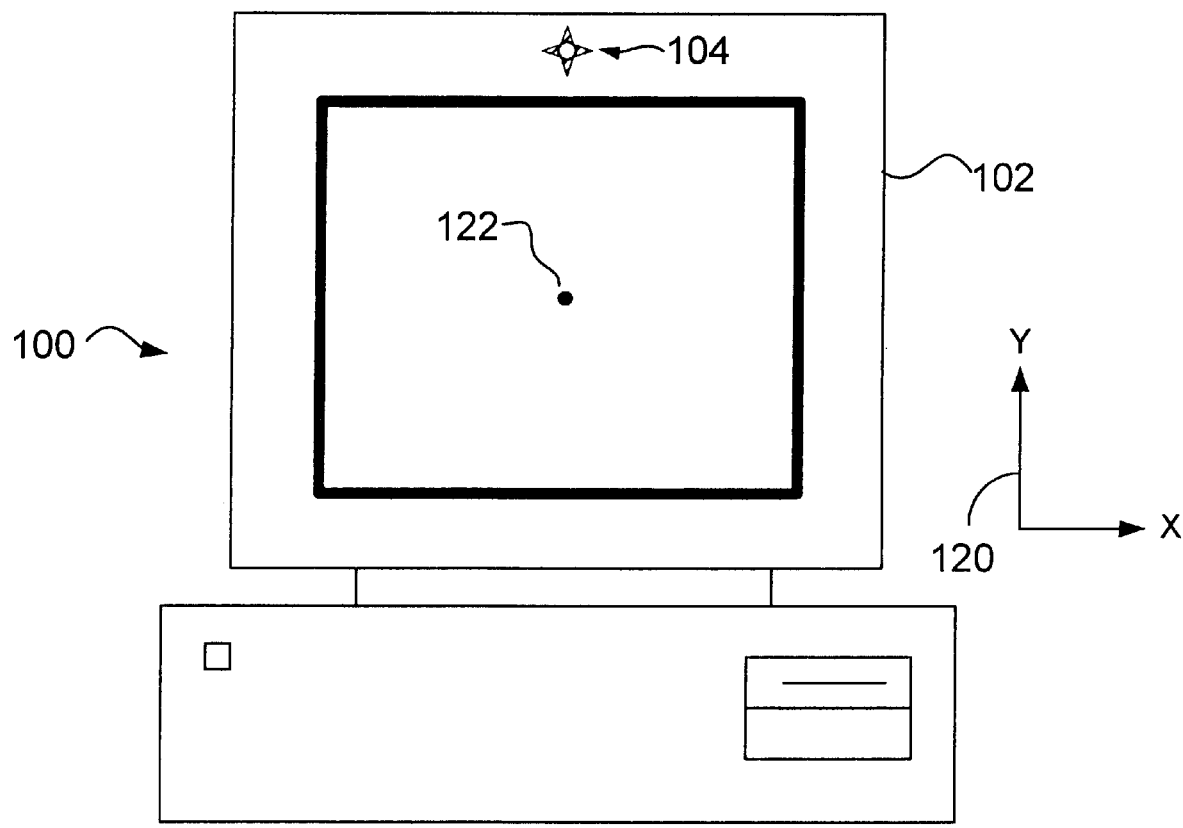
FIG. 1 illustrates a computer system having a visual feedback device in accordance with one embodiment of the present invention.

A first embodiment of the present invention will now be described with reference to FIGS. 1–5. FIG. 1 illustrates a computer system 100 including a display screen 102 and a cluster 104 (exploded in FIG. 2) of four light sources 106–112. The light sources 106–112 are arranged such that a properly oriented viewer will perceive all four light sources as illuminated. As described in more detail below with reference to FIGS 3a–5b, as the viewer's orientation varies, one or more of the light sources disappears from view, thereby indicating to the viewer that her orientation is improper.

In FIG. 1, orientation refers to a viewers position within an x-y (or horizontal-vertical) axis 120 parallel to the plane of the display panel. It has been found that a suitable orientation for a viewer of a display screen 102 is at about its top, center point. Hence in FIG. 1 the cluster 104 is located at the top, center point of the display screen 102, and is arranged such that all four lights are perceived when the viewer is substantially directly in front of the cluster 104. However, the cluster 104 may be located at a different position (on or off the display screen 102) and/or arranged to appear fully illuminated from different viewer orientations. For example, the cluster 104 may be positioned at the lower left corner of the display screen 102 yet be arranged such that all four lights are perceived when the viewer is substantially oriented at a center point 122 of the display screen.

Figure 2:
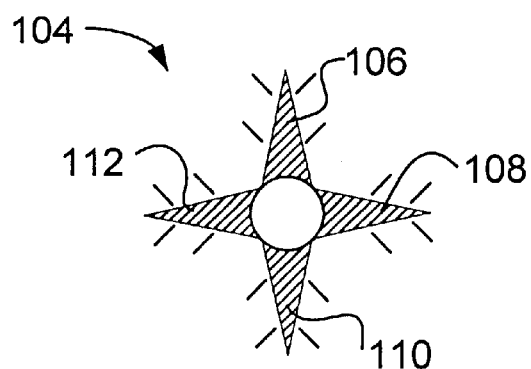
FIG. 2 illustrates a cluster of light sources forming the visual feedback device of FIG. 1.
Figures 3A, 3B:
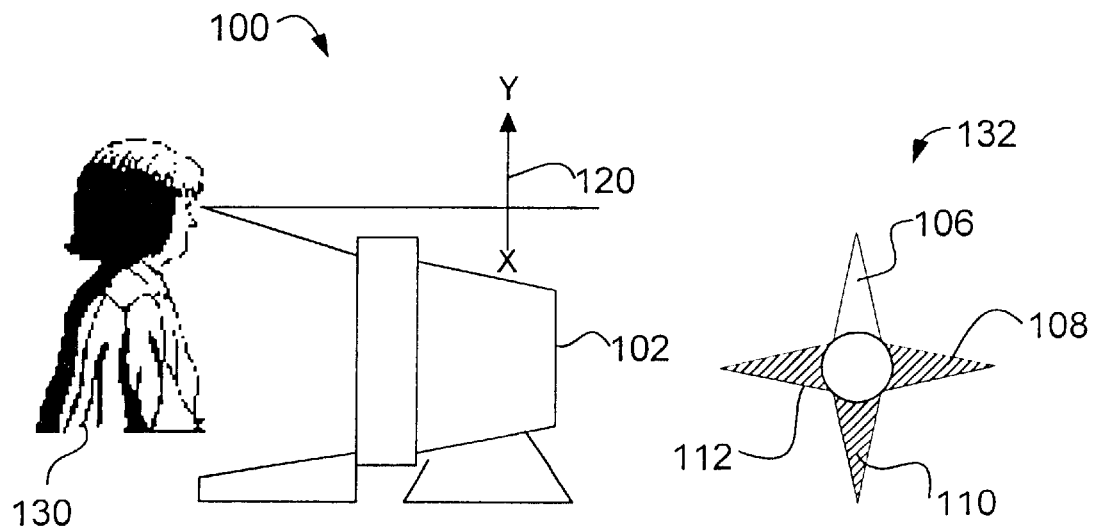
Figures 4A, 4B:
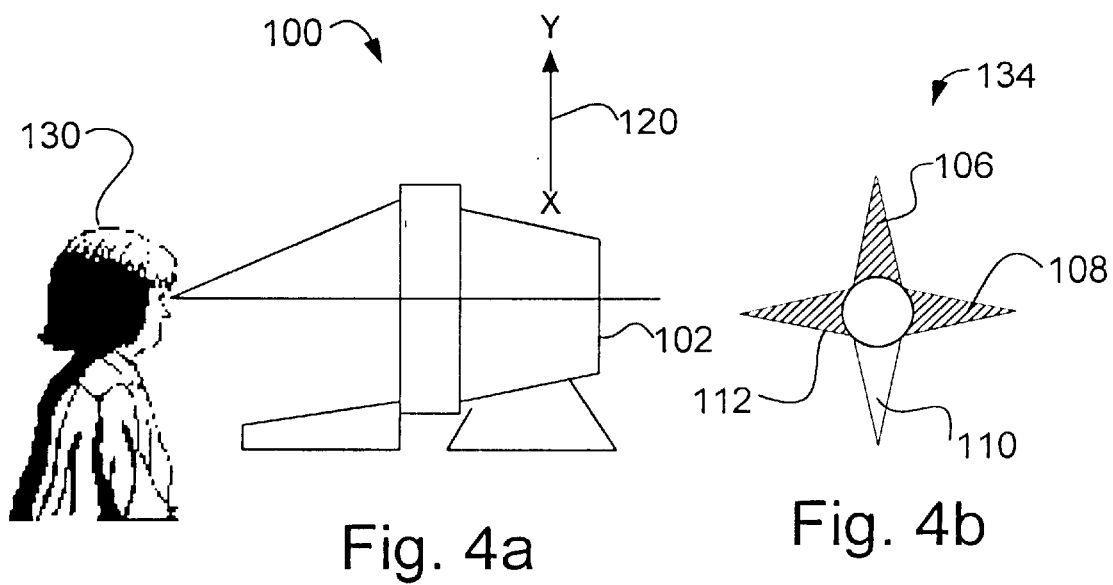
Figure 5A:
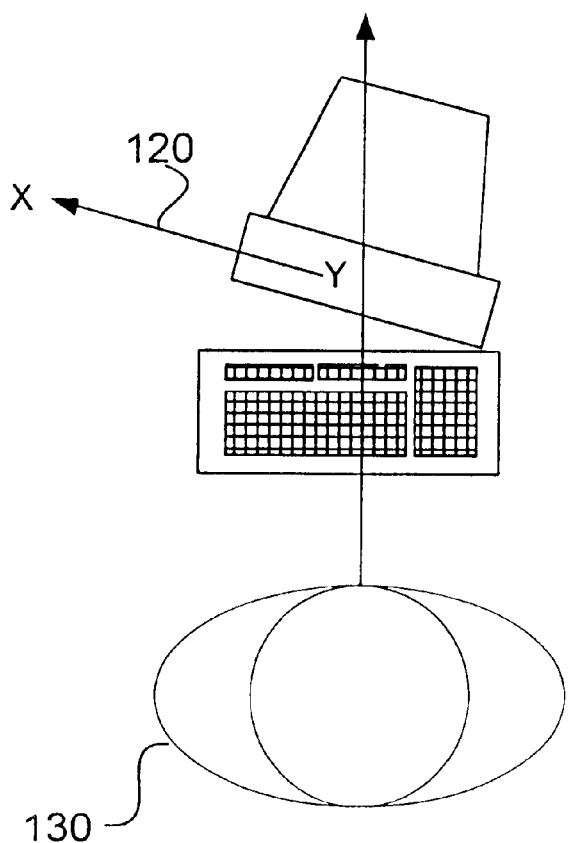
FIG. 5a illustrates a computer user positioned at an orientation off of the ideal horizontal ergonomic position.
Figure 5B:
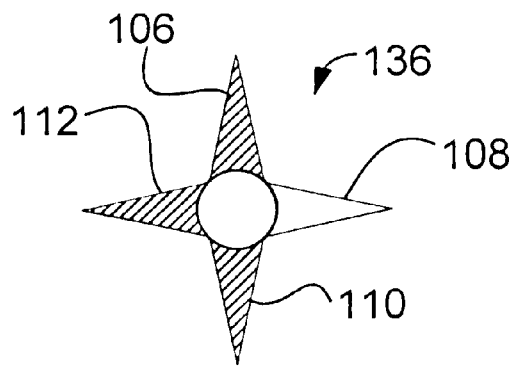

FIG. 2 illustrates the image of the cluster 104 perceived by a viewer that is properly oriented along the x-y axis 120. That is, the properly oriented viewer is capable of perceiving illumination from each of the light sources 106–112. (For the sake of present discussion, the properly oriented viewer is located near or substantially upon the origin of the x-y axis.) FIG. 3a illustrates a viewer 130 whose horizontal orientation is proper but whose vertical orientation is above the origin of the x-y axis 120. FIG. 3b illustrates an image 132 of the cluster 104 that would be perceived by the viewer 130 oriented as in FIG. 3a. Specifically, the viewer 130 perceives the cluster 104 as if the uppermost light source 106 were not illuminated. FIG. 4a illustrates the viewer 130 whose horizontal orientation is proper but whose vertical orientation is below the origin of the x-y axis 120. FIG. 4b illustrates an image 134 of the cluster 104 that would be perceived by the viewer 130 oriented as shown in FIG. 4a. Specifically, the viewer 130 perceives the cluster 104 as if the lowermost light source 110 is not illuminated. FIG. 5a illustrates the viewer 130 whose horizontal orientation is off of the origin of the x-y axis 120. FIG. 5b illustrates an image 136 of the cluster 104 that would be perceived by the viewer 130 oriented as shown in FIG. 5a. Specifically, the viewer 130 perceives the cluster 104 as if the rightmost light source 108 is not illuminated.

As will be appreciated by those skilled in the art, light sources 106–112 may take on any suitable form providing an image that varies with respect to the viewer's orientation. For example, light sources 106–112 may be light emitting sources such as LEDs or light bulbs embedded within the display screen 102, properly recessed within the display screen 102 to achieve the desired result. Alternatively, lenses covering the light emitting sources may focus or polarize the light in order to achieve the desired result. It is also contemplated that light sources 106–112 may be light reflective devices such as a hologram, a lenticular parallax panoramagram variable aspect display, other lenticular devices, diffraction grating, columnates, etc.

Alternatively, the light sources 106–112 could be four distinct pieces of diffraction grating formed such that the intensity of the reflected light varies as the viewer's orientation varies. Hence, rather than providing discrete, illuminated/non-illuminated feedback to the viewer 130, the cluster 104 could provide continuous feedback with the illumination intensity decreasing as the viewer moves further out of orientation. Alternatively, a hologram could be formed such that the image presented to the viewer changes, even presenting informative text to the viewer. (E.g., "MOVE LEFT!" or "MOVE RIGHT!") Such holograms could be implemented in many ways, whether through diffraction grating or lenticular devices.

Another aspect of the present invention teaches a feedback mechanism that provides a viewer visual feedback regarding his or her distance from the display screen. For example, a strip of diffraction grating or other suitable material applied upon the display screen may be formed such that depending upon the viewers position, the viewer perceives a feedback image (e.g., "20 Inches," a green band, a red band). Three separate embodiments of this aspect will now be described with reference to FIGS. 6–6c, FIGS. 7–8, and FIGS. 8–9, respectively.

FIG. 6 illustrates a computer system 100 having a display screen 102 with a viewer position feedback device 200 affixed thereto. The viewer position feedback device 200 is capable of presenting three images 202–206 to a viewer situated in front of the display screen 102. An image 202 as in FIG. 6a showing five filled circles 208 will be perceived by the viewer who is positioned about 18 inches (e.g., 18+/−1.0 inches) away from the display screen 102. An image 204 as in FIG. 6b showing three filled circles 208 will be perceived by the viewer who is positioned about 20 inches (e.g., 20+/−1 inches) away from the display screen. An image 206 as in FIG. 6c showing one filled circle 208 will be perceived by the viewer who is positioned about 22 inches (e.g., 22+/−1 inches) away from the display screen.

The filled circles 208 can be presented in different colors to further distinguish the distances. Outside of the optimal viewing range, the image presented by the feedback device 200 could take on any suitable form. For example, the image could be blank, provide textual information ("TOO CLOSE" or "TOO FAR"), or appear as a red strip thus indicating improper viewer positioning.

Figure 7:
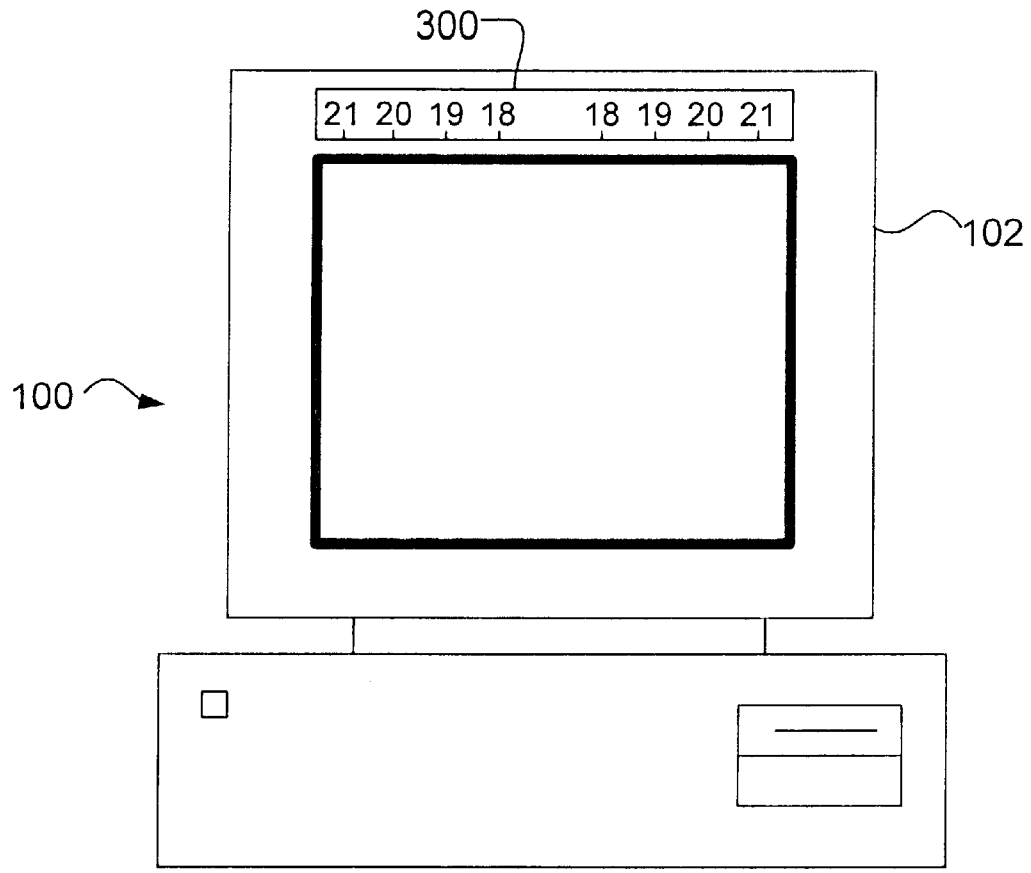
FIG. 7 illustrates a computer system having a visual feedback device in accordance with still another embodiment of the present invention, the visual feedback device capable of rendering different images dependent upon both the computer user orientation and the distance of the computer user from the computer system.
Figure 8:
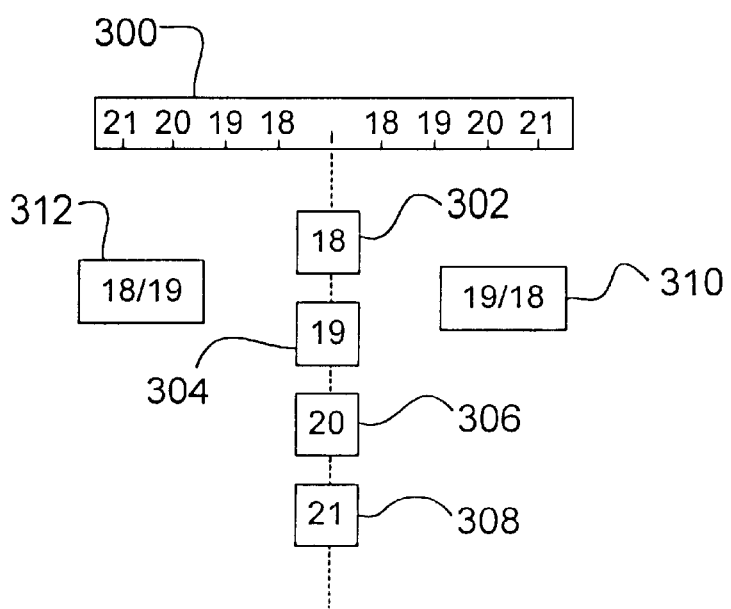
FIG. 8 illustrates several different images the computer user will perceive at different distances from and orientation to the visual feedback device of FIG. 7.

With reference to FIGS. 7–8, yet another embodiment of the present invention will now be described. FIG. 7 illustrates a computer system 100 having a display screen 102 with a viewer position and orientation feedback device 300 affixed thereto. Feedback device 300 as drawn indicates possible images for display, but does not necessarily represent how these images would be formed and arranged on the surface of feedback device 300. Instead, as will be appreciated by those skilled in the art, the arrangement of images on the feedback device will depend upon the technology (e.g., lenticular devices, diffraction grating, etc.) selected for implementation.

As illustrated in FIG. 8, the feedback device 300 is capable of presenting a plurality of images to a viewer situated in front of the display screen 102. Images 302–306 represent images perceived by the viewer when he or she is properly oriented in front of the display screen 102. For example, the image 302 appears as the numeral "18" when the viewer is properly oriented and is positioned about 18 inches from the display screen. Images 310–312 represent images perceived by a viewer improperly oriented in front of the display screen 102. For example, the image 312 appears as a combination or blurring of the numerals "18" and "19," or the image 312 may be implemented to "flicker" back and forth between the numerals depending upon slight variations of the viewer's position. In any event, the perceived image indicates to the viewer a rough estimate of her distance from the display screen 102 but, importantly, also indicates that the viewer is improperly oriented.

Figure 9:
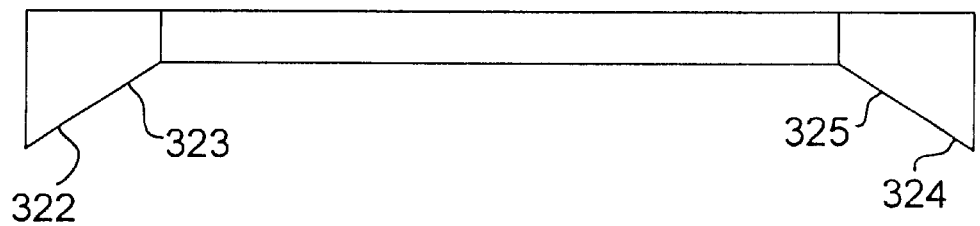
FIGS. 9–10 illustrate top and front views of a visual feedback device in accordance with yet another embodiment of the present invention.
Figure 10:
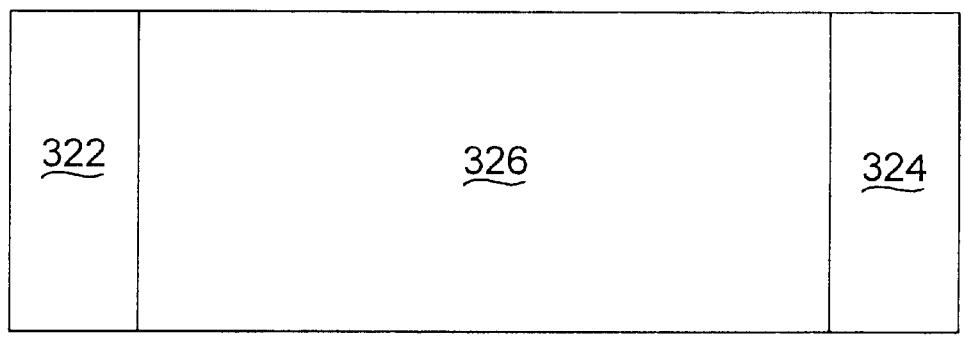

FIGS. 9–10 illustrate another embodiment of a viewer position and orientation feedback device 320 capable of providing feedback similar to that described above with reference to FIGS. 7–8. FIG. 10 provides a front-view of feedback device 320 (i.e., the view apparent to a properly situated viewer), with the active areas 322 and 324 directed towards the viewer. A center portion 326 may display a constant logo, while the active areas 322 and 324 provide the orientation and/or position feedback important to the present invention.

FIG. 9 provides a top-view of feedback device 320. As seen therein, the active areas 322 and 324 are formed having inclined surfaces 323 and 325. By selecting the angle of incline for surfaces 323 and 325 appropriately, a "sweet spot" is formed where the viewer is located in the proper orientation. The available field of view provided by active areas 322 and 324 (and thus the viewer feedback area) will depend upon the construction of and material chosen for making the active areas 322 and 324. Thus, it is preferable that the angle of incline for surfaces 323 and 325 be selected to take advantage of the available field of view. That is, the angle of incline should be selected to provide the viewer feedback in those areas were he or she would most likely be situated. However, it will be appreciated that the field of view provided by active areas 322 and 324 may be such that no incline (i.e., flat surfaces) is even necessary. In any event, those skilled in the art will understand the details necessary for selecting the suitable angle of incline and achieving the desired field of view.

Another particular embodiment that can be described with reference to FIGS. 9 and 10 is implemented such that the center portion 326 is a center active area 326. In one preferred implementation of this embodiment, the viewer feedback is accomplished through a multi-phase (animated, 3D, 4D, etc.) lenticular device. In this embodiment, the lenticular device will display a finite number of images over a suitable viewing range. For example, a total of 28 image phases over a total viewing angle of 58 degrees (i.e., plus and minus 29 degrees from the center viewing axis) would be suitable. When used with a computer monitor, for example, the feedback device 320 should be viewed in the direction of its center active area 326 at a distance of about 22 inches from within a circle having a radius of about 4 inches.

In this embodiment the center active area 326 is intended to guide the user to maintain his or her eye position near a line orthogonal to the plan of the feedback device 320 and originating at the center of the center active area 326. For example, an optimal eye position may be plus or minus 10.25 degrees from this orthogonal center line. When the user's eyes are within this optimal angle, a positive message such as "GOOD CENTER POSITION" is visible to the user within the center active area 326. As the user's eye position moves to either side of the optimal angle, a meaningful message such as "MOVE RIGHT" would become visible to the user.

The left and right active areas 322 and 324 are intended to work in conjunction with one another to guide the user in maintaining a proper distance from the feedback device 320. Viewing the right-most active area 324 from the optimal distance (e.g., about 22 inches) along the orthogonal center line, the right-most active area 324 displays a positive message such as "GOOD DISTANCE" within a predefined viewing range, e.g., a viewing angle of about 15 degrees plus or minus 10 degrees to the left of a line orthogonal to near center of the right active area 324. Outside of this range, a meaningful message such as "CHECK CENTER POSITION AND MOVE CLOSER" is displayed. The left-most active area 322 would function in an analogous manner.

The embodiments of the present invention described above are "stand alone" feedback devices that work independent of the computer system to provide real-time feedback to a user of the computer system. This feedback enables the user to achieve an ergonomic environment with respect to his or her position and orientation to the computer system. Additional aspects of the present invention further contemplate integrating the position and orientation information into ergonomic software executing upon the computer system. The ergonomic software can utilize the position and orientation information to optimize the computer system setup (e.g., display font size, brightness, etc.), as well as provide additional feedback through the computer system to the user.

Figure 11:
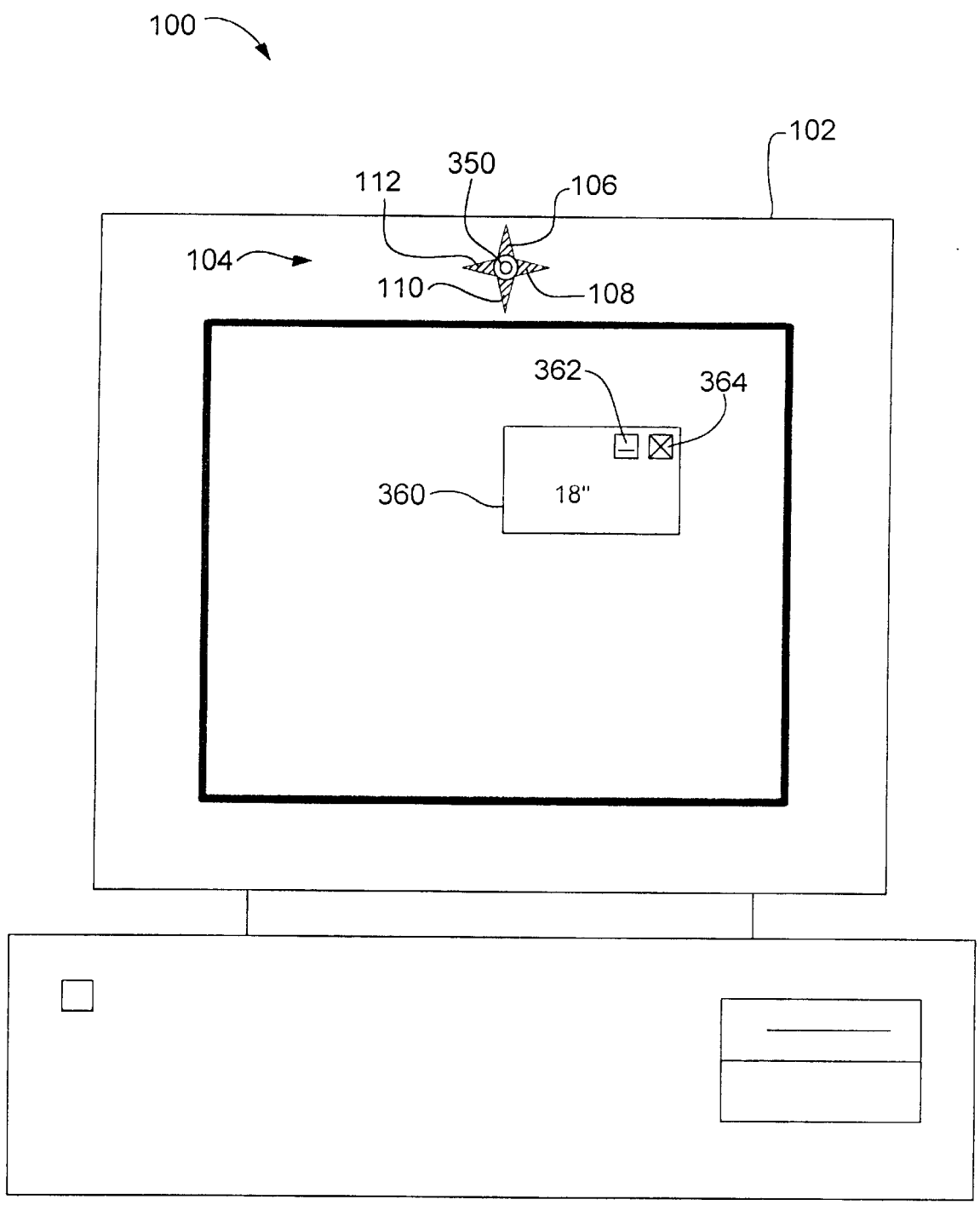
FIG. 11 illustrates a computer system having a distance position sensor in accordance with a separate embodiment of the present invention.
Figure 12:
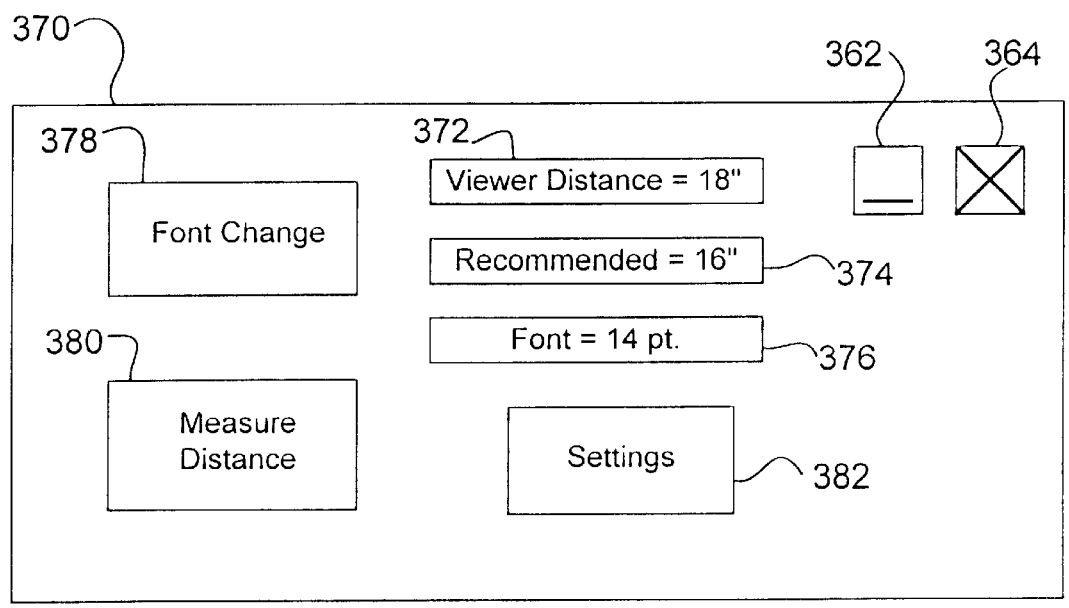
FIG. 12 illustrates an ergonomic software display window generated by the computer system of FIG. 11 when executing the ergonomic software of the present invention.

Turning to FIGS. 11–12, one embodiment of the above-described ergonomic software in accordance with the present invention will now be described. FIG. 11 illustrates a computer system 100 having a display screen 102, a cluster 104 of four light sources 106–112 embedded within the display screen 102, and a viewer position sensor 350 disposed at about the center of the cluster 104. The viewer position sensor 350 is operable to measure the distance of an object properly oriented in front of the position sensor 350. As will be appreciated, a number of such distance measurement devices exist, such as sonic and infrared measurement systems. Shown on the display screen 102 is an ergonomic software icon 360 having a minimize/maximize button 362 and a close button 364, and also a display of the viewer's position from the display screen 102.

Selecting the minimize/maximize button 362 opens up an ergonomic software window such as the window 370 shown in FIG. 12. The ergonomic software window 370 displays a viewer distance 372, a recommended viewer distance 374, a current font setting 376, a font change button 378, a measure distance button 380, and a settings button 382. The viewer distance 372 displays the most recently measured distance of the viewer from the viewer position sensor 350. For example, in certain embodiments the measurement system is continuous and the viewer distance will constantly vary with the viewer position. However, in other embodiments the viewer distance 372 will only update when the measure distance button 380 is selected.

The recommended distance 374 displays a recommended viewer position that is either provided by the ideal visual ergonomic software or can be set by the viewer through the settings button 382. The current font setting 376 preferably displays the font size of text displayed in an active window present on the display 102. Selecting the measure distance button 380 forces the position sensor 350 to measure (if possible) the distance from the viewer to the display screen 102. Once measured, the viewer distance 372 is updated and a suitable font size is selected. Selecting the font change button 378 immediately after selecting the measure distance 380 will change the font size of the corresponding text to a recommended font size based upon the viewer distance and the chosen settings.

Although only a few embodiments of the present invention have been described in detail herein, it should be understood that the present invention may be embodied in many other specific forms without departing from the spirit or scope of the invention. Therefore, the present examples are to be considered as illustrative and not restrictive, and the invention is not to be limited to the details given herein, but may be modified within the scope of the appended claims.

What is claimed is:

1. A computer implemented method for assisting a user in the control and operation of a computer system, the computer system having a display device, the computer system providing information content for display, such information content potentially containing more content such as characters, pictures, lines, or pixels than can be conveniently displayed entirely on the display device at one time, the computer implemented method comprising the acts of:

coupling a display device to a computer system;

mapping information content generated by the computer system into a virtual desktop suitable for conveying the information to the user;

displaying a certain portion of the virtual desktop using the computer system's display device;

tracking movements of the user relative to the display device; and adjusting the displayed certain portion of the virtual desktop in a manner related to the tracked movements of the display device, whereby the user is able to traverse the entire information content mapped to the virtual desktop and examine any certain portion or segment of the information content using the computer system's display device.

2. A computer implemented method as recited in claim 1 further including the acts of:

sensing a user distance from the computer user to a display screen of a computer system;

displaying the user distance on the display screen; and displaying a recommended user distance from the computer to the display screen.

3. A computer implemented method as recited in claim 2 further including the acts of:

determining a text font size deemed suitable for the user distance; and displaying a numerical indication of the text font size deemed suitable for the user distance.

4. A computer implemented method as recited in claim 3 further including the acts of:

querying a computer user as to whether to conform the font size of text found in an active text window displayed on the display screen to the text font size deemed suitable for the user distance; and in response to a request by the computer user, conforming the font size of the text found in the active text window displayed on the display screen to the text font size deemed suitable for the user distance.

5. A computer implemented method as recited in claim 3 further including the act of conforming the font size of text found in an active text window displayed on the display screen to the text font size deemed suitable for the user distance.

6. A computer implemented method as recited in claim 2 wherein the act of sensing a user distance from the computer user to a display screen of a computer system is performed continuously.

7. A computer implemented method as recited in claim 6 wherein the displayed user distance is updated continuously.

8. A computer implemented method as recited in claim 2 wherein the act of sensing a user distance from the computer user to a display screen of a computer system is performed only in response to a request from the computer user.

9. A method for visually navigating a virtual map generated by a physical map application executing upon a computer system, the computer system having a display device and a user position sensor, the method comprising the acts of:

transforming visual information generated by the physical map application into a virtual map suitable for display via the display device;

displaying a certain portion of the virtual map via the display device;

tracking movements of the user relative to the computer system; and updating the displayed certain portion of the virtual map in a manner correlated to the tracked movement of the user.

10. A computer implemented method as recited in claim 9 further comprising the act of redefining the orientation of the certain portion displayed via the display device such that, without moving the hand held computer system, the certain portion displayed via the display device changes.

11. A computer implemented method as recited in claim 9 wherein the orientation of the certain portion displayed is redefined in response to a request by a user.

12. A computer implemented method as recited in claim 9 wherein a virtual magnification of the displayed certain portion is updated in a manner correlated to the tracked movement of the user.

13. A computer implemented method as recited in claim 9 wherein a virtual magnification of the displayed certain portion is updated in response to a command entered into the computer system by a user.

14. A computer implemented method as recited in claim 9 wherein the navigation capability of the physical map includes a scalability feature allowing adjustment of the scalability of the physical map in order to provide a viewer of the display device views of the physical map having different magnifications.

15. A computer system comprising:
   a digital processor;
   a user position detector referenced to a user position and coupled to a display device;
   the display device coupled to the digital processor; and
   a computer readable medium coupled to the digital processor, the computer readable medium having computer executable instructions for:
      mapping visual information generated by the computer system into a virtual desktop suitable for display via the display device;
      displaying a certain portion of the virtual desktop via the display device;
      tracking movement of the user relative to the computer system via the motion detector; and
      updating the displayed certain portion of the virtual desktop in a manner correlated to the tracked movement of the computer system.

16. A hand computer system as recited in claim 15 wherein a first window of the multiple application windows corresponds to a first application executing upon the computer system.

17. A hand held computer system as recited in claim 16 wherein the first application executing upon the computer system is a physical map application.

18. A hand held computer system as recited in claim 17 wherein the physical map application enables navigation through a physical map via user movement of the display device.

19. A hand held computer system as recited in claim 15 wherein the displayed certain portion of the virtual desktop is adjusted in a manner related to the tracked movements of the display device in relation to a substantially planar surface.

20. A hand held computer system as recited in claim 19 wherein the computer readable medium further comprises computer executable instructions for updating a virtual magnification of the displayed certain portion in response to a command entered into the computer system by a user of the computer system.

* * * * *